US 6,640,412 B2

(12) United States Patent
Iancea (10) Patent No.: US 6,640,412 B2
(45) Date of Patent: Nov. 4, 2003

(54) METHOD FOR LOADING A STENT USING A COLLAPSING MACHINE

(75) Inventor: Octavian Iancea, Fremont, CA (US)

(73) Assignee: Endovascular Technologies, Inc., Santa Clara, CA (US)

(*) Notice: Subject to any disclaimer, the term of this patent is extended or adjusted under 35 U.S.C. 154(b) by 220 days.

(21) Appl. No.: 09/844,865

(22) Filed: Apr. 26, 2001

(65) Prior Publication Data

US 2002/0161426 A1 Oct. 31, 2002

(51) Int. Cl.$^7$ ................................................ B23P 11/00
(52) U.S. Cl. .............................. 29/505; 29/516; 29/282; 29/283.5
(58) Field of Search ........................ 29/505, 506, 508, 29/516, 517, 520, 234, 235, 280, 282, 281.4, 283.5; 623/1.11, 1.12, 1.18, 1.19, 1.2; 606/108

(56) References Cited

U.S. PATENT DOCUMENTS

| | | |
|---|---|---|
| 696,289 A | 3/1902 | Williams |
| 2,964,088 A | 12/1960 | Erath |
| 4,455,854 A | 6/1984 | Ermolovich |
| 4,468,224 A | 8/1984 | Enzmann et al. |
| 4,546,646 A | 10/1985 | Williams et al. |
| 4,576,142 A | 3/1986 | Schiff |
| 4,644,936 A | 2/1987 | Schiff |
| 4,681,092 A | 7/1987 | Cho et al. |
| 4,697,573 A | 10/1987 | Schiff |
| 4,901,707 A | 2/1990 | Schiff |
| 4,907,336 A | 3/1990 | Gianturco |
| 5,132,066 A | 7/1992 | Charlesworth et al. |
| 5,133,732 A | 7/1992 | Wiktor |
| 5,183,085 A | 2/1993 | Timmermans |
| 5,189,786 A | 3/1993 | Ishikawa et al. |
| 5,437,083 A | 8/1995 | Williams et al. |
| 5,546,646 A | 8/1996 | Williams et al. |
| 5,626,604 A | 5/1997 | Cottone, Jr. |

(List continued on next page.)

FOREIGN PATENT DOCUMENTS

| | | |
|---|---|---|
| DE | 464004 | 8/1928 |
| EP | 0 630 623 A2 | 12/1994 |
| EP | 0 826 346 A1 | 3/1998 |
| EP | 0 873 731 A1 | 10/1998 |
| EP | 0 938 877 A2 | 9/1999 |
| GB | 159065 | 2/1921 |
| WO | WO 98/14120 | 4/1998 |
| WO | WO 98/19633 | 5/1998 |

OTHER PUBLICATIONS

The eXTraordinary Stent, C.R. Bard Brochure (undated).

Primary Examiner—Gregory Vidovich
Assistant Examiner—Jermie E. Cozart
(74) Attorney, Agent, or Firm—Fulwider Patton Lee & Utecht, LLP (57) ABSTRACT

A machine for collapsing a stent and loading the same into a delivery catheter is disclosed. The stent collapsing machine includes an elongate base plate, a belt having a first end and a second end, and a first and second sliding plate slidably mounted to the elongate base plate. A first belt mount may be affixed to the first sliding plate and a second belt mount affixed to the elongate base plate, each belt mount having a bottom piece and a top piece for tightly securing the belt first end and second end. A jaw block set is mounted to the second sliding plate, the jaw block set having a first jaw block and a jaw block sliding plate with a second jaw block mounted thereon. The jaw block sliding plate allows the second jaw block to be slidably translated in relation to the first jaw block. The belt is allowed to rest over the first and second jaw block thereby forming a belt loop therebetween for receiving a stent. At least one actuating mechanism may be mounted on the elongate base plate and attached to the first end of the belt for providing a force upon the belt thereby collapsing the belt loop having the stent therein.

5 Claims, 6 Drawing Sheets

U.S. PATENT DOCUMENTS

| | | |
|---|---|---|
| 5,630,830 A | 5/1997 | Verbeek |
| 5,653,691 A | 8/1997 | Rupp et al. |
| 5,672,169 A | 9/1997 | Verbeek |
| 5,693,066 A | 12/1997 | Rupp et al. |
| 5,725,519 A | 3/1998 | Penner et al. |
| 5,738,674 A | 4/1998 | Williams et al. |
| 5,746,764 A | 5/1998 | Green et al. |
| 5,759,474 A | 6/1998 | Rupp et al. |
| 5,782,855 A | 7/1998 | Lau et al. |
| 5,782,903 A | 7/1998 | Wiktor |
| 5,783,227 A | 7/1998 | Dunham |
| 5,785,715 A | 7/1998 | Schatz |
| 5,787,572 A | 8/1998 | Toms |
| 5,810,838 A | 9/1998 | Solar |
| 5,810,871 A | 9/1998 | Tuckey et al. |
| 5,810,873 A | 9/1998 | Morales |
| 5,836,952 A | 11/1998 | Davis et al. |
| 5,893,852 A | 4/1999 | Morales et al. |
| 5,893,867 A | 4/1999 | Bagaoisan et al. |
| 5,920,975 A | 7/1999 | Morales |
| 5,931,851 A | 8/1999 | Morales |
| 5,944,735 A | 8/1999 | Green et al. |
| 5,947,993 A | 9/1999 | Morales |
| 5,948,191 A | 9/1999 | Solovay |
| 5,951,569 A | 9/1999 | Tuckey et al. |
| 5,972,016 A | 10/1999 | Morales |
| 5,974,652 A | 11/1999 | Kimes et al. |
| 6,009,614 A | 1/2000 | Morales |
| 6,024,737 A | 2/2000 | Morales |
| 6,051,002 A | 4/2000 | Morales |
| 6,063,092 A | 5/2000 | Shin |
| 6,063,102 A | 5/2000 | Morales |
| 6,074,381 A | 6/2000 | Dinh et al. |
| 6,092,273 A | 7/2000 | Villareall |
| 6,125,523 A | 10/2000 | Brown et al. |
| 6,141,855 A | 11/2000 | Morales |
| 6,245,100 B1 | 6/2001 | Davila et al. |

METHOD FOR LOADING A STENT USING A COLLAPSING MACHINE

BACKGROUND OF THE INVENTION

The present invention relates to an apparatus for loading a tubular graft, such as a stent, onto the distal end of a catheter assembly of the kind used, for example, in percutaneous transluminal coronary angioplasty (PTCA) or percutaneous transluminal angioplasty (PTA) procedures.

Prior art stents typically fall into two general categories of construction. A first type of stent is expandable upon application of a controlled force, for example, through the inflation of the balloon portion of a dilatation catheter which, upon inflation of the balloon or other expansion means, expands the compressed stent to a larger diameter to be left in place within the artery at the target site. A second type of stent is a self-expanding stent formed from, for example, shape memory metals or super-elastic nickel-titanium (NiTi) alloys, which will automatically expand from a compressed state when the stent is advanced out of the distal end of the delivery catheter into the body lumen. Such stents manufactured from expandable heat sensitive materials allow for phase transformations of the material to occur, resulting in the expansion and contraction of the stent.

Generally, in typical PTCA procedures, a guiding catheter is percutaneously introduced into the cardiovascular system of a patient through the brachial or femoral arteries and advanced through the vasculature until the distal end of the guiding catheter is in the ostium. A guide wire and a dilatation catheter having a balloon on the distal end are introduced through the guiding catheter with the guide wire sliding within the dilatation catheter. The guide wire is first advanced out of the guiding catheter into the patient's coronary vasculature and the dilatation catheter is advanced over the previously advanced guide wire until the dilatation balloon is properly positioned across the arterial lesion. Once in position across the lesion, a flexible and expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

In angioplasty procedures of the kind referenced above, restenosis of the artery may develop over time, which may require another angioplasty procedure, a surgical bypass operation, or some other method of repairing or strengthening the area. To reduce the likelihood of the development of restenosis and to strengthen the area, a physician can implant an intravascular prosthesis for maintaining vascular patency, commonly known as a stent, inside the artery at the lesion. The stent is transported through the patient's vasculature to the implant site where it is to be deployed. At the implant site, the stent is expanded to a larger diameter. For a self-expanding sent, deployment is achieved by allowing the stent to be released from a delivery catheter where upon freedom from the constraints of the delivery catheter the stent self-expands. Alternatively for a balloon expandable stent, deployment is achieved by inflating a balloon portion of a dilatation catheter forcing expansion of the stent.

Because the catheter and stent must travel through the patient's vasculature, and possibly through the coronary arteries, the stent must have a small delivery diameter and must be firmly secured within a delivery catheter until the physician is ready to implant it. Thus, the stent must be loaded onto the catheter so that it does not interfere with delivery, and it must not come off the catheter until it is implanted.

In procedures where a self-expanding stent is utilized, the stent is placed within a protective delivery sleeve of the delivery catheter. It is necessary to properly collapse the stent for loading into the protective delivery sleeve. This collapsing of the stent has proven to be a particular challenge where it is necessary to load the stent into a small diameter delivery catheter. Because of the inherent tendency for a self-expanding stent to resist compression, it is difficult to ensure a uniform collapse of the stent during the loading process without possible damage to or improper orientation of the stent. The resistance to compression is especially pronounced where it is necessary to load the stent into a small diameter delivery catheter because the stent must be collapsed down to an extremely small profile.

In procedures where a balloon expandable stent is utilized, the stent is placed over the balloon portion of the catheter, it is necessary to crimp the stent onto the balloon portion to reduce its diameter and to prevent it from sliding off the catheter when the catheter is advanced through the patient's vasculature. Nonuniform crimping can result in sharp edges being formed along the now uneven surface of the crimped stent. Furthermore, non-uniform stent crimping may not achieve the desired minimal profile for the stent and catheter assembly. Where the stent is not reliably crimped onto the catheter, on rare occasions it is possible that the stent may slide off the catheter and into the patient's vasculature prematurely as a loose foreign body, possibly causing blood clots in the vasculature, including thrombosis. Therefore, it is important to ensure the proper crimping of a stent onto the balloon portion of a catheter in a uniform and reliable manner.

It is generally the case that the collapsing or crimping of a stent is often done by hand, which can be unsatisfactory due to the uneven application of force resulting in non-uniform collapsing or crimps. In addition, it is difficult to visually judge when a uniform and reliable crimp has been applied.

As mentioned above, the problem often encountered with hand loading self-expanding stents into a delivery catheter is that given the natural tendency of self-expanding stents to expand back to an expanded profile. Upon compressing the stent for loading onto a catheter, the stent will quickly spring out of a compressed state thereby making it a cumbersome ordeal. Unlike balloon expandable stents that hug or grip the balloon in which the stent has been crimped, in order to successfully load a compressed self expanding stent a need exists for a collapsing device that will maintain the compressed state of the stent until it is successfully loaded within a protective delivery sleeve of a delivery catheter. Again, the difficulty in loading such a stent is increased where it is desirous to further reduce the stent's compressed profile for loading onto smaller diameter catheters. Furthermore, the more the stent is handled the higher the likelihood of human error. Accordingly, there is a need in the art for a device that will reliably collapse a stent and allow it to be loaded into a smaller low profile delivery catheter.

There have been attempts at devising a tool for compressing a stent, most of which have been directed to the crimping of a balloon expandable stent onto a balloon delivery catheter. An example of such a tool embodies a series of plates having substantially flat and parallel surfaces that move in a rectilinear fashion with respect to each other. A stent carrying catheter is disposed between these surfaces, which surfaces crimp the stent onto the outside of the catheter by their relative motion and applied pressure. The plates have multiple degrees of freedom and may have force-indicating transducers to measure and indicate the force applied to the catheter during crimping of the stent.

Another stent loading tool design includes a tubular member housing a bladder. The tubular member and bladder are constructed to hold a stent that is to be crimped onto a balloon catheter assembly. Upon placement of the stent over the balloon portion of the catheter, a valve in the loading tool is activated to inflate the bladder. The bladder compresses the stent radially inward to a reduced diameter onto the balloon portion of the catheter to achieve a snug fit. In this way, the stent is crimped onto the distal end of a balloon catheter with a minimum of human handling.

Yet another stent crimping tool known in the art is constructed from a rigid, tubular body with a ball at one end connected to a plurality of long, thin strips passing through the tubular body. An uncrimped stent is placed over the plurality of long, thin strips, which hold the stent in an expanded state. The balloon portion of a catheter is inserted into the cylindrical space formed by the plurality of strips. When the user pulls the ball while holding the tubular body against the stent, the strips are slid from beneath the stent and the stent is transferred onto the balloon portion.

Still another conventional stent crimping tool appears similar to a hinged nutcracker. Specifically, the tool includes two hand operated levers hinged at one end and gripped in the palm of the hand at the opposite end. A cylindrical opening holding a crimping tube is provided through the mid-portion of the tool to receive therein a stent loaded onto a balloon catheter. The crimping operation is performed by the user squeezing the handle thereby pressing the crimping tube which in turn pinches the stent onto the balloon catheter.

While the prior art devices discussed above are suitable for and generally directed to crimping a typical balloon expandable stent onto a balloon catheter, they may not be suitable for collapsing and loading a self-expanding stent due to the tendency of such a stent to expand during the loading process. Additionally, because of this natural tendency to resist compression, prior art devices directed to crimping balloon expandable stents, when applied to self-expanding stents can suffer from problems such as non-uniform compressing forces, resulting in nonuniform collapsing. Consequently, what is needed is a device to collapse balloon expanded or self-expanding stents and load them into a low profile delivery catheter.

SUMMARY OF THE INVENTION

The present invention is directed to a collapsing tool that can repeatedly provide a uniform and tight collapse of a stent to ensure the low profile diameter of the stent in a compressed state for placement into a delivery catheter. More specifically, the present invention is directed to a collapsing machine that can compress a stent and properly load the same into a protective sleeve of a delivery catheter. The invention also provides a uniform compression force that is capable of maintaining a self-expanding stent in a compressed state therefore ensuring a minimized profile during the loading of the stent into a small diameter delivery catheter, thereby ensuring that the stent is properly loaded with minimum human intervention.

In a preferred embodiment, the present invention is directed to a machine for compressing a stent and loading it into a delivery catheter. The machine includes an elongate base plate having a top surface, a first end and a second end and a belt having a first end and a second end. A first and second sliding plate is slidably mounted to the elongate base plate top surface. A first belt mount may be affixed to the first sliding plate and a second belt mount may be affixed to the second end of the elongate base plate and each belt mount includes a bottom piece and a top piece for tightly securing the belt first end and the second end thereto. Additionally, a jaw block set is provided, the jaw block set includes a first jaw block and a second jaw block. The first jaw block may be stationarily mounted to the second sliding plate and a jaw block sliding plate having the second jaw block mounted thereon may also be slidably mounted to the second sliding plate at a position adjacent to the first jaw block. The jaw block sliding plate allows the second jaw block mounted thereon to be slidably translated back and forth in relation to the first jaw block.

The first and second jaw block define a top opening into the space in between the first and second jaw blocks. Once the belt is mounted onto the elongate base plate, the belt mid-portion is allowed to rest over the first and second jaw block and any lag occurring from the loosely mounted belt may be used to form a belt loop positioned within the jaw block set—in between the first and second jaw block for receiving a stent. Finally, the machine includes at least one actuating mechanism mounted on the elongate base plate top surface and the actuating mechanism is attached to the first end of the belt for providing a force unto the belt thereby pulling taut the loosely mounted belt. With a stent mounted within the belt loop, when the belt is pulled taut, the belt loop collapses thereby collapsing the stent placed therein.

The present collapsing machine invention is capable of imparting a radial pressure onto the stent work piece positioned within the belt loop by pulling taut the belt thereby compressing the belt loop thus collapsing the stent-support pin therebetween. The belt action evenly distributes the collapsing pressure to obtain a homogeneous and uniform collapse along the circumference of the stent.

In another preferred embodiment of the present invention, the machine further includes multiple jaw block sets. Two or more jaw block sets, each set having a first jaw block and a second jaw block mounted and configured in the same manner as the jaw block set discussed above may be mounted upon the elongate base plate. The number of jaw block sets which may be included in this configuration may be limited only by the desired length of the elongate base plate or by the desired length of the belt. This embodiment operates in much the same way as the first preferred embodiment and allows for the simultaneous collapsing and loading of multiple stent work pieces. It is contemplated that this embodiment will be particularly useful for purposes of mass production.

In yet another embodiment of the present invention, the machine further includes a second actuating mechanism. This second actuating mechanism provides for force to be applied to the belt at both of the belt ends thereby allowing for more pulling force to be applied during the stent collapsing procedure. This added component is especially useful when utilized in conjunction with the second preferred embodiment having multiple jaw block sets for simultaneously collapsing multiple stents because in such a situation, more pulling force may be desirable to adequately collapse all of the stents simultaneously.

During use, along with the collapsing machine as described above, a support pin may also be provided. The support pin includes a first section and a second section, the first section having a smaller diameter than the second section, and the first section and the second section is connected at a point defining a beveled step between the first section and the second section. The smaller first section of the support pin may be placed within an expanded stent to be collapsed and the entire stent-support pin assembly may then be inserted into the belt loop of the collapsing machine. Once inserted, the second jaw block may be positioned relative the first jaw block such that the belt loop top opening defined by the first and second jaw blocks is substantially pinched or closed off.

With the un-collapsed stent having the smaller first section of the support pin inserted therein positioned properly within the belt loop, the belt loop may be collapsed thereby collapsing the stent about smaller first section of the support pin. Finally, the support pin may be used to push the collapsed stent and load it into a low profile delivery catheter. This is accomplished by pushing the support pin until the beveled edge makes contact with and pushes upon the collapsed stent. Further pushing of the support pin will force the collapsed stent out of the collapsed belt loop and with a low profile delivery catheter in proper position, the collapsed stent may be pushed out of the belt loop and translated directly into the low profile delivery catheter thereby completing the loading process once the support pin is withdrawn from the now loaded stent.

The present invention collapsing machine is thus highly useful to cardiologists, for example. Such physicians are constantly concerned with proper deployment of the stent within the patient, especially where vessels become smaller and smaller, and it is desirable to have as small as possible a stent profile for loading into a very small stent delivery catheter. The present invention is further a time saver in that the stent collapsing procedure can be performed fairly efficiently and quickly. As such, the machine may further be used for production collapsing and loading of self-expanding stent designs. These and other advantages of the present invention will become apparent from the following detailed description thereof when taken in conjunction with the accompanying exemplary drawings.

DETAILED DESCRIPTION OF THE PREFERRED EMBODIMENTS

Figure 1:
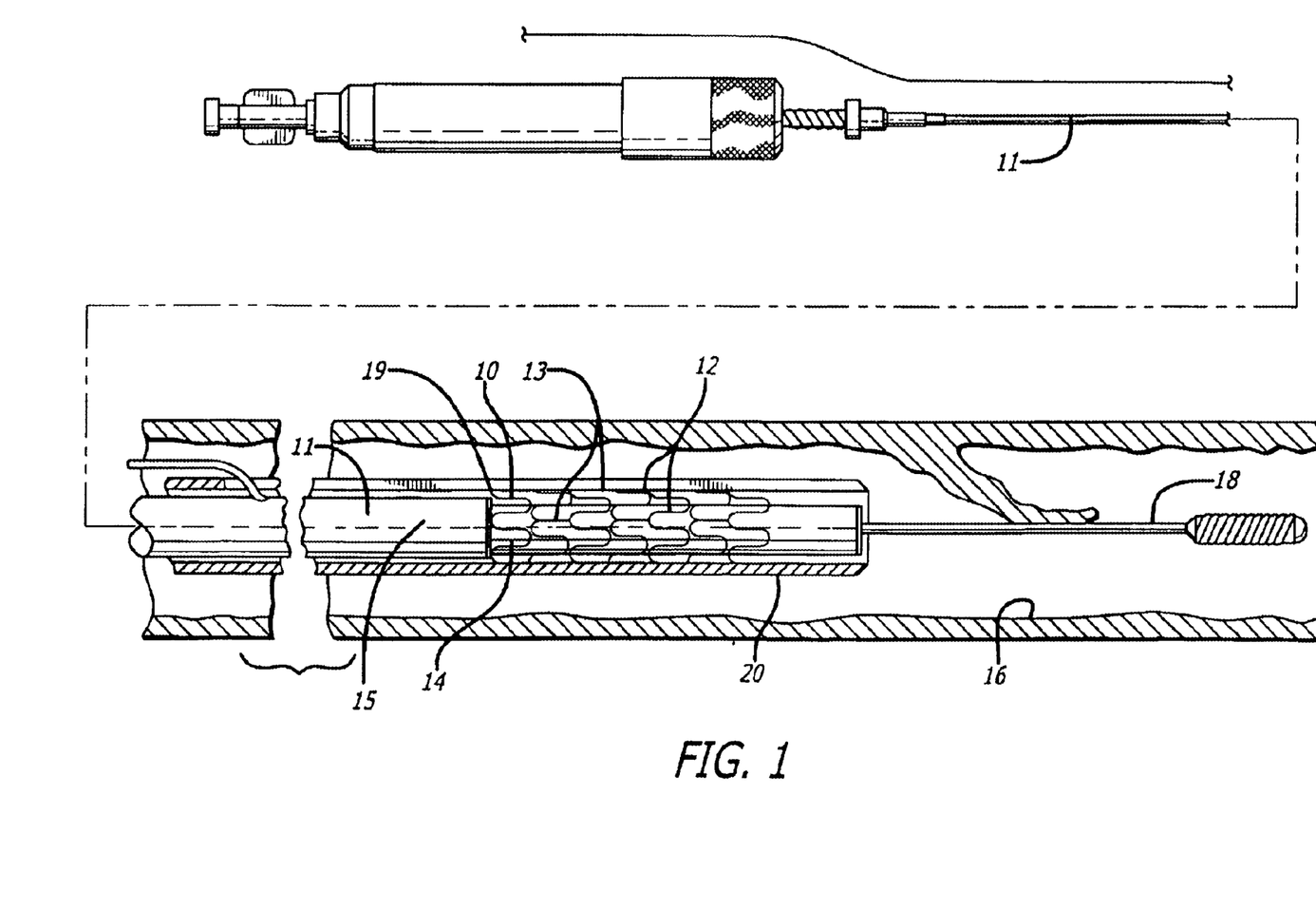
FIG. 1 is a side elevational view, partially in section, depicting a self-expanding stent that has been collapsed and loaded into a delivery catheter and disposed within a damaged vessel.

FIG. 1 illustrates an intravascular stent 10 which is mounted onto a delivery catheter 11. The stent 10 generally embodies a plurality of radially expandable cylindrical elements 12 disposed generally coaxially and interconnected by members 13 disposed between adjacent cylindrical elements 12. The delivery catheter 11 may include two sections—a first section 14 and a second section 15, each section having a different cross-sectional diameter. The catheter first section 14 has a diameter smaller than the second section 15 and may be of a length equal or slightly longer than one stent 10 length. Because the catheter first section 14 will have a diameter smaller then the second section 15, a step 19 is formed where the two sections 14, 15 of the catheter are joined.

The delivery catheter 11 further includes a retractable protective delivery sleeve 20 which may encompass the entire length of the catheter 11. The protective delivery sleeve may be slidably moved proximally and distally in relation to catheter 11. Once loaded, the stent 10 is disposed within the protective delivery sleeve 20 of the catheter 11 to ensure that the stent 10 remains in a compressed form and to prevent abrasion of the body lumen by the open surface of the stent 10 during delivery to the desired arterial location. Primarily directed to use with self-expanding stents, the protective delivery sleeve 20 also serves to maintain the stent 10 in a compressed state during delivery until deployment is desired. In order to implant the stent 10, it is first loaded within the protective delivery sleeve 20 and disposed about the smaller first section 14 of the catheter 11. In this delivery configuration, the proximal edge of the stent may butt up against the step 19 of the catheter 11.

During delivery of the apparatus within a damaged vessel such as saphenous veins, carotid arteries, or other arteries or veins, the edge of the stent 10 may be maintained against the step 19. Upon reaching the deployment site within the damaged vessel, the step 19 serves to maintain the relative position of the stent 10 as the protective delivery sleeve 20 is retracted proximally in relation to the catheter 11. Upon retraction of the protective delivery sleeve 20, the stent is allowed to be exposed and therefore will self expand and be deployed within the damaged vessel 16 that may have a dissected lining or other disease or abnormality which has occluded a portion of the arterial passageway.

Delivery catheter 11 having a protective delivery sleeve 20 into which stent 10 is loaded is known in the art and is essentially the same as a conventional delivery catheter for angioplasty procedures. In order for the stent 10 to be loaded into the protective delivery sleeve 20 of the catheter 11, the stent 10 is compressed about the smaller distal section 14 of the delivery catheter 11. This compressing step is known as collapsing.

The stent-catheter assembly can be introduced into the patient's vasculature through processes known in the art. Briefly, a guide wire 18 is disposed across the arterial section where an angioplasty or atherectomy has been performed requiring a follow-up stenting procedure. In some cases, the arterial wall lining may be detached so that the guide wire 18 is advanced past the diseased portion and the stent-catheter assembly is advanced over the guide wire 18 within the artery 16 until the stent 10 is directly under the diseased portion.

Prior to deployment of the stent 10, the protective delivery sleeve 20 is retracted proximally to expose the stent 10. As the protective sleeve 20 is retracted in relation to the delivery catheter 11, the stent 10 maintained therein in a compressed state will naturally expand back to its original un-compressed state and therefore expand against the vessel wall. Optionally, an expandable balloon catheter may be used to further secure the stent within the vessel (not shown) or employed to deliver and deform a balloon expandable stent.

Figure 2A:
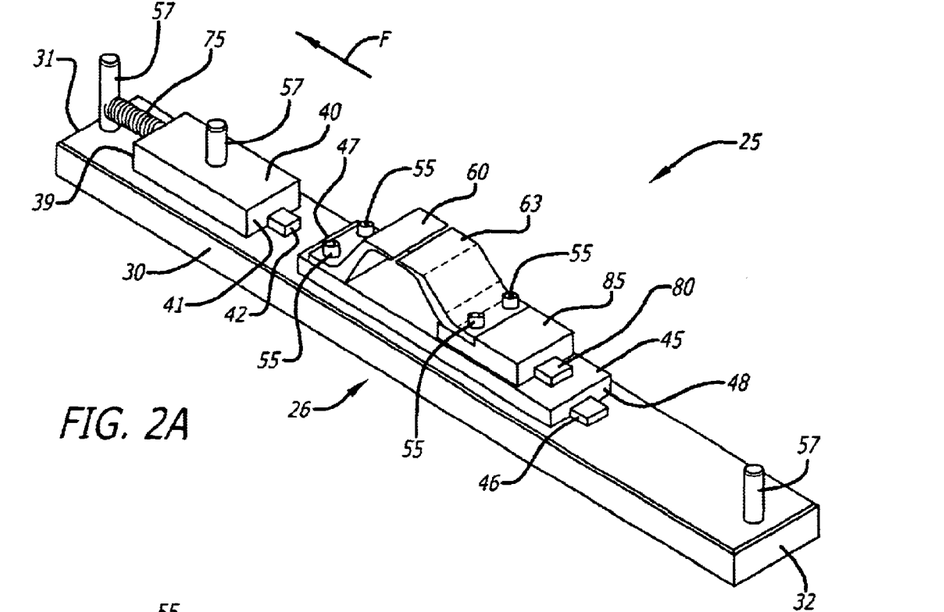
FIG. 2A is a perspective view, depicting the preferred embodiment of the present collapsing machine without a belt mounted thereon.
Figure 2B:
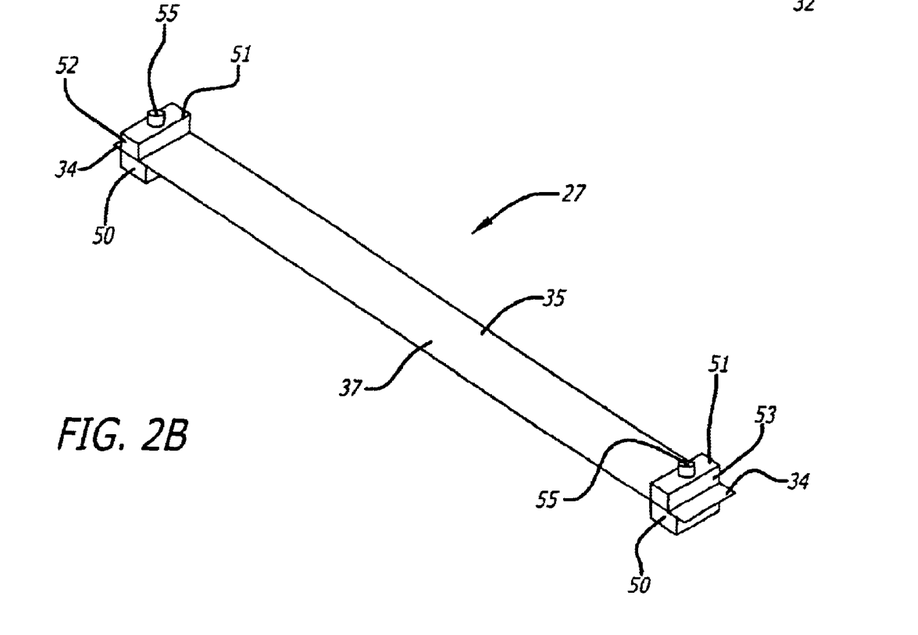
FIG. 2B is a perspective view, depicting the belt having mounts clamped on each of the belt ends for use with the portion of the collapsing machine of FIG. 2A.

Referring to FIGS. 2A and 2B, there is depicted a perspective view of a preferred embodiment of the present stent collapsing machine 25. Specifically, the present invention is directed to a collapsing machine 25 for collapsing an intra-vascular stent 10 for placement into a protective delivery sleeve 20 of a delivery catheter 11. The present invention is particularly useful for collapsing a self-expanding stent such as a nitinol stent. In such a case, the present invention allows for a self-expanding stent to be collapsed and easily loaded into a delivery catheter assembly. However, it is noted that the present collapsing machine invention may also be used to crimp a balloon-expandable stent such as a stainless steel, cobalt-chromium or platinum-iridium stent onto a balloon catheter.

Referring to FIGS. 2A and 2B, the present device 25 includes two major parts, a base piece 26 (FIG. 2A) and a belt piece 27 (FIG. 2B). Referring in particular to FIG. 2A, the stent collapsing machine base piece 26 includes an elongate rectangular shape base plate 30 having a first end 31 and a second end 32. Additionally, a first sliding plate 40 and a second sliding plate 45 may be slidably mounted to the elongate rectangular shape base plate 30 such that the first sliding plate may be positioned near the base plate first end 31 and the second sliding plate may be positioned somewhere between the first sliding plate and the base plate second end 32. The first sliding plate 40 cooperates with a rail piece 42 that is securely mounted to the elongate base plate 30. The rail piece 42 allows the first sliding plate 40 to smoothly glide back and forth along a longitudinal axis of the elongate base plate 30. Similarly, the second sliding plate 45 cooperates with a second rail piece 46 that is securely mounted to the base plate 30 and allows the second sliding plate 45 to smoothly glide back and forth along the longitudinal axis of the elongate base plate 30.

The first sliding plate 40 includes a first end 39 and a second end 41, wherein the sliding plate first end is connected to an actuation mechanism 75, which may be, for example, a spring or any other mechanism providing a lateral force F. The spring 75 is connected on one end to the first end 39 of the first sliding plate 40, and on the other end to a pin mount 57 affixed to the elongate base plate 40 at a location adjacent to the base plate first end 31. The first sliding plate 40 further includes a mount pin 57 extending perpendicular to the top surface of the first sliding base plate 40.

It is noted that the actuating mechanism used herein may be embodied in a spring or a pneumatically operated piston within a cylinder. The actuator 75 can be manually operated, lever operated, pneumatically operated, or triggered by a similar technology known in the art in order to generate the lateral force F. Primarily, the actuator 75 would be used as a time saving measure for high cyclic rates in a production line for example. Moreover, a machine generated lateral force would be uniform and controlled so that very precise collapsing of a stent 10 can be achieved.

Referring still to FIG. 2A, the second sliding plate 45 includes a first end 47 and a second end 48 and is slidably mounted on the elongate base plate 30 at a location between the first sliding plate 40 and the elongate base plate second end 32.

A jaw block set having a first jaw block 60 and a second jaw block 63 may be positioned atop the second sliding plate 45. The first jaw block 60 is stationarily affixed to the second sliding plate 45 by a pair of lugs 55. The first jaw block 60 is affixed atop the second sliding plate 45 near the second sliding plate first end 47. The second jaw block 63 is stationarily affixed to a slide block 85 by a pair of lugs 55. The slide block 85 is slidably mounted to the second sliding plate 45 and cooperates with a rail 80 affixed to the second sliding plate 45 at a position between the first jaw block 60 and the second end 48 of the second sliding plate 45. The rail 80 allows the slide block 85 having the second jaw block 63 mounted thereon to smoothly glide back and forth with respects to the second sliding plate 45. The slide block 85 may be locked into a desired position upon the second sliding plate 85 by any means of securing known in the art (not shown).

Finally, the base piece 26 includes another mount pin 57 affixed to the elongate base plate 30 at a location near the elongate base plate second end 32. This mount pin 57 and the mount pin 57 located atop the first sliding plate 40 allows for a belt piece to (to be described hereinafter) to be attached to the base piece 26.

Referring now to FIG. 2B, the other major component of the stent collapsing machine 25 is a belt piece 27 that includes an elongate belt 35 having opposing end portions 34 and amid-portion 37. The belt 35 maybe constructed from a flexible material, such as Mylar or a woven fabric having a smooth finish. A first mount assembly 52 and second mount assembly 53 are also provided, both mount assemblies having a bottom piece 50, a top piece 51 and a lug 55 for clamping down and tightly securing the end portions 34 of the belt 35. At each mount 52 and 53, the belt end portions 34 are clamped between bottom piece 50 and top piece 51 and secured by tightening lug 55. Additionally, the mount bottom piece 50 has a hole (not shown) extending from bottom of the mount bottom piece for receiving pins 57 located on the base piece 26 as described above.

Figure 3:
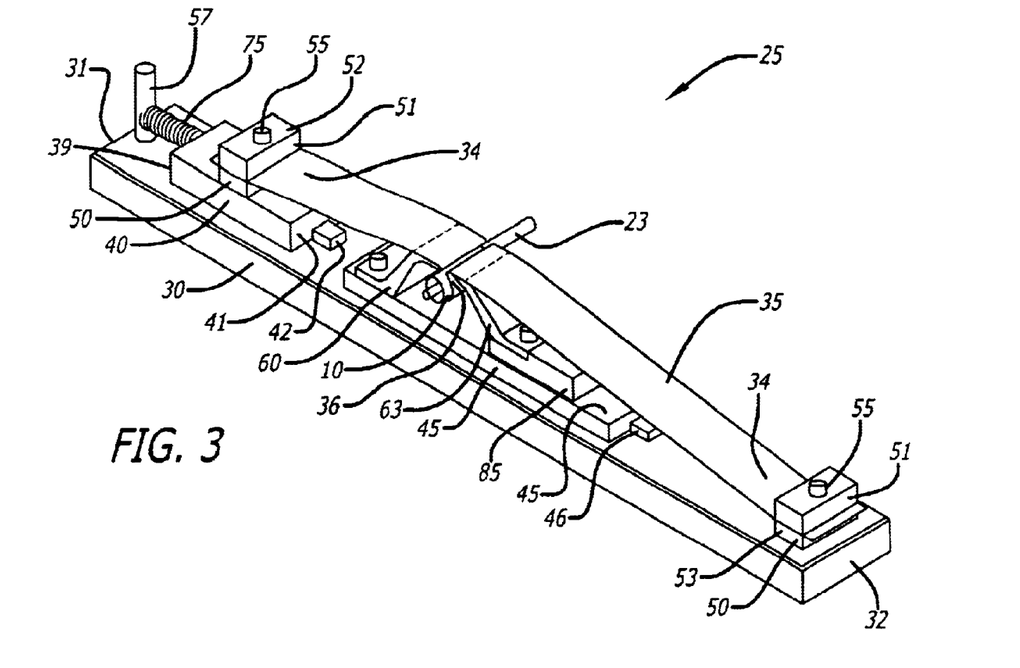
FIG. 3 is a perspective view, depicting a preferred embodiment of the present collapsing machine.

Referring to FIG. 3, the various parts of the device—the base piece 26 and the belt piece 27 are connected such that the mounts 52 and 53, having the belt end portions 34 clamped therein, are attached to the elongate base plate 30. The first mount 52, may be spaced apart from the second mount 53 and attached over pin 57 on the first sliding plate 40 situated at one end, preferably the first end 31, of the elongate base plate 30. The second mount 53 may be attached over pin 57 situated adjacent to the second edge 32 of the elongate base plate 30. The belt mid-portion 37 may loosely rest upon the first and second jaw blocks 60 and 63. The belt mid-portion 37, being loosely mounted to the base piece 26 may form a belt loop 36 between the first and second jaw blocks 60 and 63 for receiving a stent to be collapsed. The belt loop 36 is formed from the gravitational slack created when the belt 35 is loosely laid to rest upon the jaw blocks 60 and 63, the more slack that is available on the belt the bigger the loop 36 may be. In general, the loop 36 should initially be of generous size, forming a loop having a circumferential size large enough to easily receive a stent 10 in its expanded first diameter.

Figure 4:
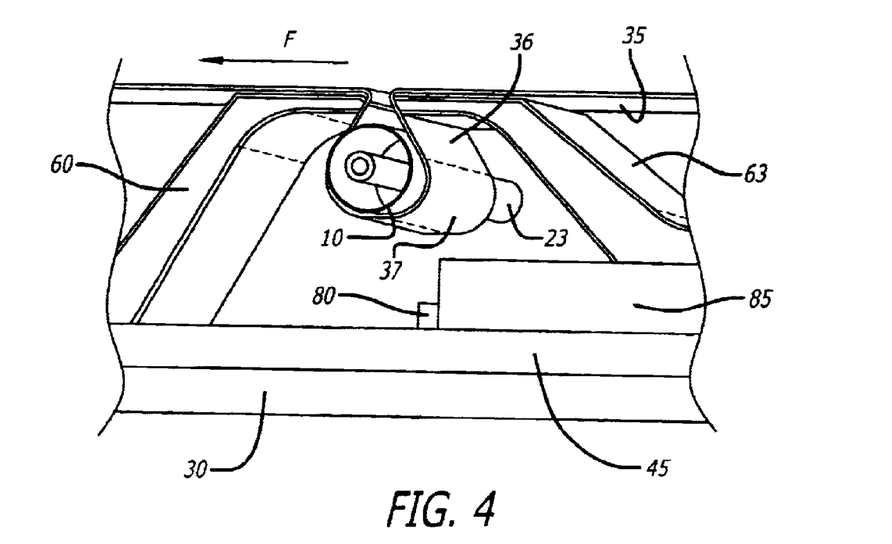
FIG. 4 is a close up, perspective view, depicting the preferred embodiment in accordance with the present invention.

Referring to FIG. 4, an enlarged view of the collapsing machine is provided, depicting the first and second jaw blocks 60 and 63 with a belt loop 36, formed from the belt 35 mid-section 37, having a stent 10 disposed therein. When the flexible belt 35 is pulled taut in a predetermined direction represented by arrow F, the size of loop 36 is uniformly decreased and a radially collapsing force is introduced upon the outer circumference of the stent 10 causing it to collapse upon a first section 22 of a support pin 23. The support pin utilized herein will be subsequently described in further detail. As the belt is pulled taut to a predetermined tightness, a given amount of radial force is provided to collapse the stent 10 upon the support pin 23 until it is well collapsed thereon.

Figure 5:
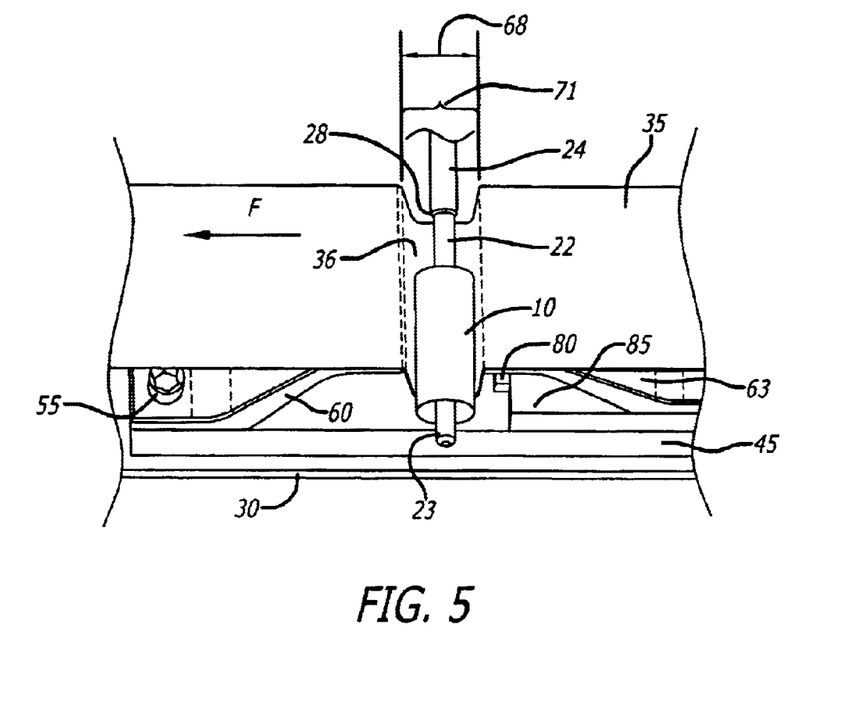
FIG. 5 is a top perspective view, depicting the preferred embodiment having a first gap between a pair of jaw blocks providing an opening into a belt loop for receiving a stent.
Figure 6:
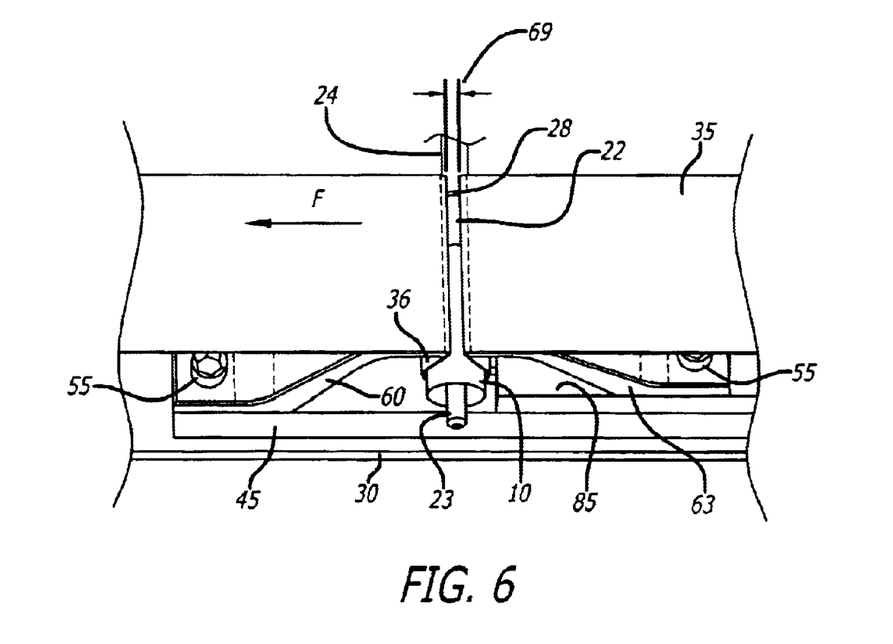
FIG. 6 is a top perspective view, depicting the preferred embodiment having a second gap between a pair of jaw blocks during the collapsing process, the second gap substantially smaller than the first gap of FIG. 4, which allows for the belt loop to substantially enclose and encompass a stent.

Referring to FIGS. 5 and 6, in accordance with the present invention, a method of collapsing a self-expanding stent is provided. To use the present invention, the cardiologist or user may prepare the collapsing machine by securing the opposing end portions 34 of the belt 35 to a first mount 52 and a second mount 53. The belt ends 34 may be secured by clamping the belt end in between the mount bottom piece 50 and mount top piece 51 and then tightly securing the entire mount with a lug 55 (see FIG. 2B).

Once the belt end portions 34 are secured to the first mount piece 52 and second mount pieces 53, the belt 35 may be positioned upon the base piece 26 (see FIG. 3). This is accomplished by aligning and placing the mount bottom piece 50, which includes a hole, onto pins 57 of the base piece as described above. After the belt piece 27 and base piece 26 are connected, the collapsing machine 25 is ready for use. During actual use, it may be beneficial to initially mount only one end of the belt. Preferably the second mount 53 onto the pin 57 located near the second end 32 of the elongate base plate 30, leaving the other end of the belt, which is clamped within mount 52, unattached to the elongate base plate 30 until a later time in the procedure. This step will provide the necessary belt looseness or slack for proper placement of a stent onto the collapsing machine as will be discussed shortly.

Referring to FIG. 5, the user may then choose a stent to be collapsed. Depending on the size of the stent to be collapsed, the collapsing machine may be prepared adequately. For example, given a particular stent 10 having an expanded profile, the second jaw block 63 may be positioned and spaced apart from the first jaw block 60, thereby forming a first gap 68 between the first and second jaw blocks. The first gap 68 should be such that the stent, in an expanded configuration, may be easily loaded into the collapsing machine 25. Once the jaw blocks are adequately spaced, the belt mid-portion 37 may be placed down into the gap 68 and therein the belt mid-portion 37 may be manipulated to form a belt loop 36 within the space between the first and second jaw blocks 60 and 63. The formed belt loop 36 will have a top opening 71 allowing access into the belt loop for placement of the stent 10 to be collapsed. This step may be easily accomplished because the belt piece 27 has not yet been fully mounted, with the first mount 52, so far, unattached to pin 57 of the first sliding plate 40 located near the first end 31 of the elongate base plate 30 and therefore the belt 35 is not taut, allowing easy manipulation. Once the belt loop 36 is formed, the stent 10 may be placed therein.

Upon placement of the stent within the belt loop 36, a support pin 23 may be inserted into the center of the stent to support the stent structure upon collapsing the stent. Additionally, the support pin 23 will serve to load the stent into a delivery catheter as will be described hereinafter. The support pin 23 may be a solid shaft and may include two sections—a first section 22 and a second section 24, each section having a different cross-sectional diameter. The support pin first section 22 has a diameter smaller than the second section 24 and may be of a length equal to the width of the belt 35. The support pin second section 24 will have a diameter greater than the first section 22 and a step 28 is formed where the two sections of the support pins are joined. The support pin 23 may be placed within the center of the stent such that the stent, when collapsed, will tightly surround the support pin first section 22 with the edge of the stent 10 nearly butting up against the step 28 of the support pin. Thereafter, the step 28 formed by the bigger edge of the support pin second section 24 may be used to push the collapsed stent 10 and load it into a delivery catheter 20.

Referring to FIG. 6, after the stent 10 is placed within the belt loop 36, the second jaw block 63 may be moved closer to the first jaw block 60 and locked into place by any feasible locking mechanism (not shown), thereby minimizing the first gap 68 and forming a second, substantially smaller gap 69. This step closes or pinches together the belt loop top opening 71 and provides a circular containment of the stent 10 within the belt loop 36. The second gap 69 should be small enough such that it will pinch down the belt loop 36 and there will only be enough space for the belt 35 to have free movement in and out of the gap 69.

After the second jaw block 63 is positioned and locked into place to ensure proper enclosure of the belt loop 36 about the stent 10 and support pin 23, the first end portion 34 of the belt 35, already secured to the first mount 52, as described above, may be affixed to the pin 57 of the first sliding plate 40. The stent is now properly positioned within the collapsing device and ready for collapsing.

Figure 7:
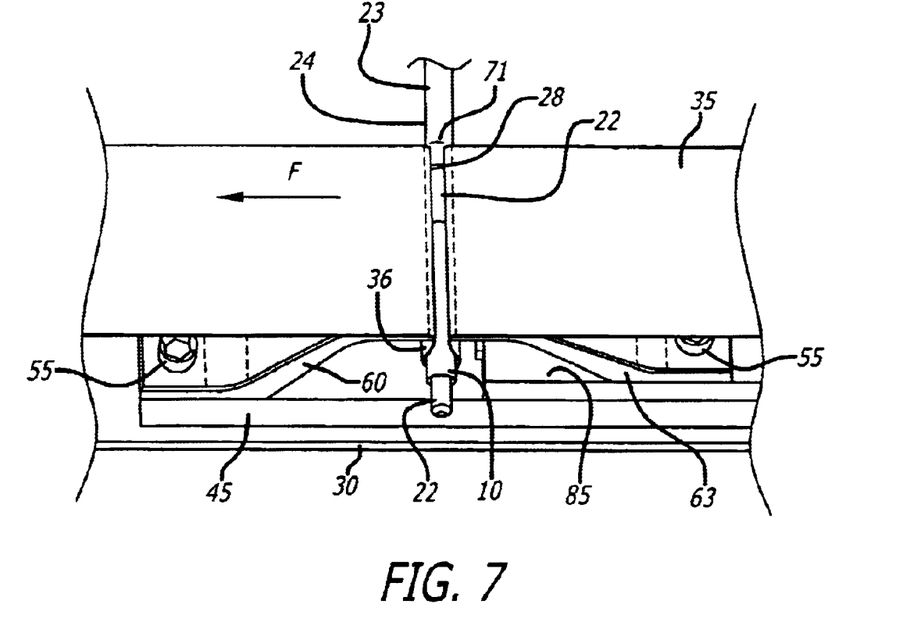
FIG. 7 is a top perspective view, depicting a collapsed stent within the belt loop.

In order to collapse the stent, an actuation device may be activated, for example, a spring 75 attached to the first edge 39 of the sliding plate 40 (see FIG. 3) may be allowed to recoil and thereby apply a force F (see FIG. 4) pulling one edge of the belt 35 out of the top opening 71. Because of the substantially closed top opening 71 defined by gap 69, the belt will be pulled up, however, the stent 10 having the support pin inserted therein will not be able to be pulled through the substantially closed top opening 71. Therefore, as shown in FIG. 7, the belt loop 36 will gradually shrink and in the process collapse the stent 10 positioned therein. The belt loop 36 will continue to shrink until the stent is snugly collapsed about the smaller first section 22 of the support pin 23.

Figure 8:
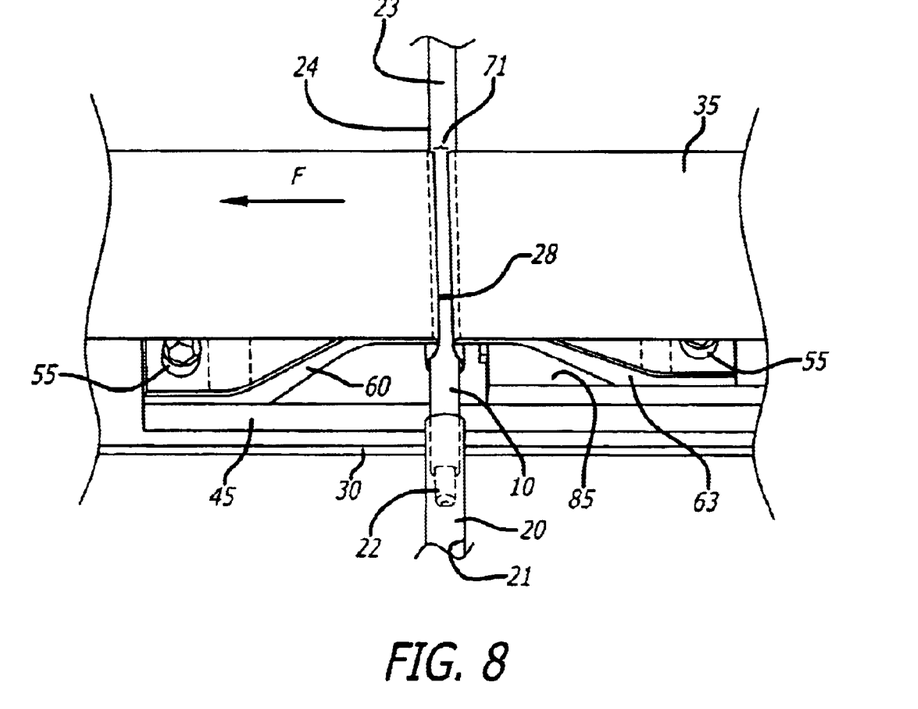
FIG. 8 is a top perspective view, depicting a collapsed stent being loaded into a delivery catheter in accordance with the current invention.

Referring now to FIG. 8, once the stent 10 is collapsed within the belt loop 36, it may be loaded into a protective delivery sleeve 20. This is accomplished by pushing the support pin 23 forward. With the beveled step 28 engaged to the edge of the collapsed stent 10, the forward pushing of the support pin 23 will force the collapsed stent out of the belt loop 36. Having the protective delivery sleeve 20 positioned to receive the collapsed stent 10, the stent may be transferred from within the belt loop 36 into a hollow lumen 21 of the protective delivery sleeve 20 by forward pushing the collapsed stent with the support pin. Once inserted into the protective delivery sleeve 20, the collapsed stent may slightly expand due to it's natural tendency to return to its uncompressed state. However, because it is enclosed within the protective delivery sleeve it will be contained therein in a compressed state and ready for delivery into the human vasculature.

Figure 9:
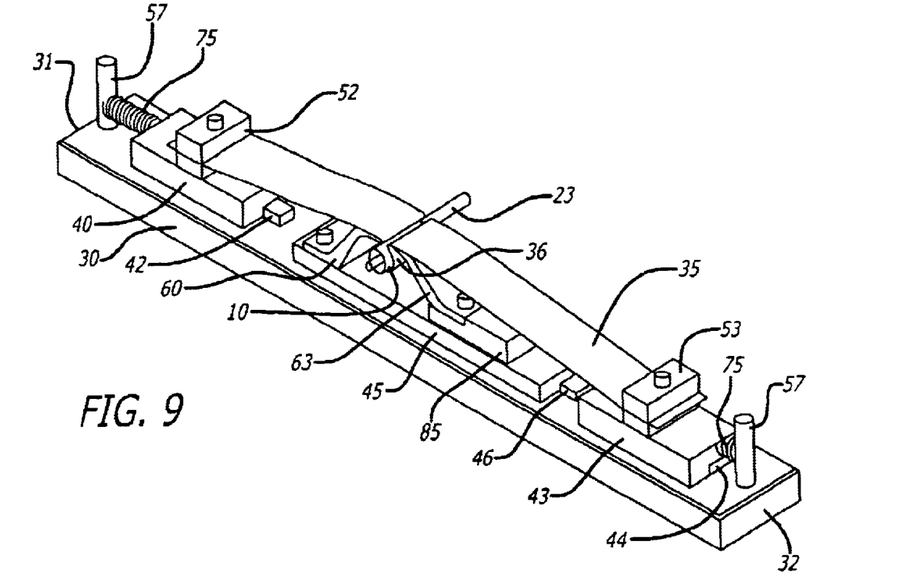
FIG. 9 is a perspective view, depicting an alternative embodiment of the present invention including dual actuating mechanisms.

Referring to FIG. 9, in an alternative embodiment of the current invention, the collapsing machine may include more than one actuation device. In addition to the first actuation device 75 positioned near the first end 31 of the elongate base plate 30, there may also be available a second actuation device attached to the second end 32 of elongate base plate 30. In such an embodiment, the second mount 53 may be attached to a sliding plate 43 that cooperates with a rail piece 44 stationarily affixed to the elongate base plate 30 at a position near the elongate base plate second end 32. The sliding plate 43 and rail piece 44 may be connected to the elongate base plate 30 in a similar fashion as the first sliding plate 40 and first rail piece 42 as discussed above. Also sliding plate 43 may serve the same function as the first sliding plate 40, which is to allow the second belt mount 53 freedom of sliding motion given the force exerted by the second actuation device 75. This embodiment may provide a uniform pulling of the belt on both ends of the belt thereby reducing the wear and tear upon stationary portions of the belt through repeated uses of the current invention.

Figure 10:
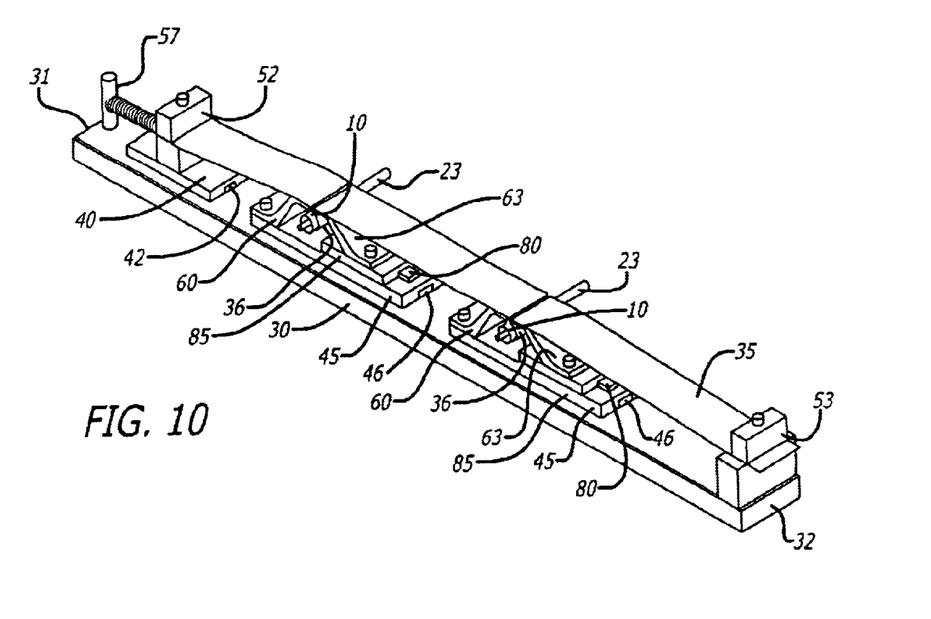
FIG. 10 is a perspective view, depicting yet another alternative embodiment of the present invention including a second set of jaw blocks for collapsing multiple stents simultaneously.

Referring now to FIG. 10, another novel and important feature of the current invention is its ease of adaptability for use in collapsing multiple stents simultaneously. The elongate base plate 30 may be of any length and may include multiple sets of adjustable jaw blocks. A set of jaw blocks may include a first jaw block 60 and a second jaw block 63 configured as described above. For example, a second set of adjustable jaw blocks may be affixed onto the elongate base plate 30 in tandem with the first set of adjustable jaw blocks. In such a configuration the belt 35 would be positioned to form two belt loops 36, one within each of the space defined by the adjustable jaw block sets. Therefore, in this exemplary configuration, applying the use steps as described above, the present invention is capable of simultaneously collapsing two stents. It will be understood by one skilled in the art that this multiple configuration may be expanded for use in collapsing any number of stents and is limited only by the length of the base plate 30 and the length of belt 35. It is noted that his configuration may incorporate the use of multiple actuation devices as was the case in the previous embodiment.

The present invention is sterilized and intended to be used in a cath lab by a trained technician or cardiologist. More precisely, as is appreciated by those skilled in the art, that the present invention collapsing machine 25 is designed both for single use applications in a cath lab by a physician, single use in a manufacturing facility, or for multiple use applications in a sterile environment in a high volume manufacturing facility for example. In such a manufacturing facility where sterile conditions exist, the stent collapsing machine 25 can be used repeatedly to collapse and load stents into delivery catheters until the belt 35 wears out. In such a case the belt may be replaced and operations may be continued. Thus, repeated uses of the present invention are contemplated for controlled, sterile, environments, as are single use applications when operated by cath lab personnel. The present invention can be used in a cold box environment such that the ambient environment around the nitinol stent is sufficiently cold to transform the material from its austenitic phase to its martensitic phase before the present invention is used to collapse the stent. Alternatively, or in addition, the present invention can have orifices located in one or both of the jaw blocks on either side of the stent in the loop that direct a cold gas such as liquid nitrogen onto the stent to accomplish the phase transformation before the stent is collapsed.

Furthermore, the present invention collapsing machine can be used with any stent that is released without a delivery system. The collapsing machine may also be sold alone, because its design is robust enough to undergo many uses.

Other modifications can be made to the present invention without departing from the scope thereof. The specific dimensions, procedural steps, and materials of construction are provided as examples, and substitutes are readily contemplated which do not depart from the invention.

What is claimed is:

1. A method for loading a stent into a delivery catheter using a collapsing machine having an elongate base plate, a belt, a jaw block set having a first and second jaw block, an actuating mechanism and a support pin having a first section and a second section, the first section having a smaller diameter than the second section and the first section and the second section being connected at a point defining a beveled step between the first section and the second section, comprising:

placing the support pin first section within an expanded stent to be collapsed;

positioning the stent and support pin assembly into a loop formed from the belt resting over the jaw block set of the collapsing machine;

securing the second jaw block to a position relative the first jaw block such that a belt loop top opening is defined by the first and second jaw blocks;

collapsing the stent positioned within the belt loop; and loading the collapsed stent onto a delivery catheter.

2. The method for loading a stent according to claim 1, the step of collapsing the stent further comprising initiating the actuating mechanism to apply a force on a first end of the belt, thereby collapsing the belt loop located between the first and second jaw blocks.

3. The method for loading a stent according to claim 1, wherein the step of loading the stent further includes pushing the support pin having a beveled step to force the collapsed stent into a delivery catheter.

4. The method for loading a stent according to claim 1, wherein the collapsing machine includes a cold box and further comprising lowering the temperature in the cold box to transform material embodying the stent from an austenitic phase to a martensitic phase.

5. The method for loading a stent according to claim 1, wherein the collapsing machine includes orifices configured to receive a cold gas and further comprising exposing the stent to the cold gas in order to accomplish a phase transformation.

* * * * *